(12) United States Patent
Kaneblei

(10) Patent No.: US 11,557,915 B2
(45) Date of Patent: Jan. 17, 2023

(54) MOBILE MEASURING DEVICE WITH A POWER SUPPLY MODULE AND PROCESS FOR POWER SUPPLY

(71) Applicant: Dräger Safety AG & Co. KGaA, Lübeck (DE)

(72) Inventor: Ingo Kaneblei, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 267 days.

(21) Appl. No.: 16/941,848

(22) Filed: Jul. 29, 2020

(65) Prior Publication Data
US 2021/0036542 A1 Feb. 4, 2021

(30) Foreign Application Priority Data
Jul. 31, 2019 (DE) .......................... 102019005358.3

(51) Int. Cl.
*H02J 7/35* (2006.01)
*H02J 50/10* (2016.01)
*G01N 33/00* (2006.01)

(52) U.S. Cl.
CPC ............ *H02J 7/35* (2013.01); *G01N 33/0009* (2013.01); *H02J 50/10* (2016.02)

(58) Field of Classification Search
CPC ......... H02J 7/35; H02J 50/10; G01N 33/0009
USPC .......................................................... 73/23.2
See application file for complete search history.

(56) References Cited

U.S. PATENT DOCUMENTS

| | | | |
|---|---|---|---|
| 7,395,692 B2 | 7/2008 | Wansing | |
| 10,015,658 B1* | 7/2018 | Alfaro | H04W 88/06 |
| 10,191,023 B2 | 1/2019 | Bather et al. | |
| 10,795,420 B2* | 10/2020 | Wilhelmi | G06F 1/263 |
| 2008/0197801 A1* | 8/2008 | Manor | H02J 7/342 |
| | | | 320/103 |
| 2011/0278937 A1* | 11/2011 | Patino | G06F 1/263 |
| | | | 307/80 |
| 2014/0062191 A1* | 3/2014 | Bryson | H02J 1/12 |
| | | | 307/26 |
| 2014/0375280 A1* | 12/2014 | Jung | H02J 7/0029 |
| | | | 320/163 |
| 2016/0241048 A1* | 8/2016 | Badam | H01M 50/247 |
| 2016/0248125 A1* | 8/2016 | Huang | H01M 10/4207 |
| 2018/0109126 A1* | 4/2018 | Gavriliu | H01M 10/4257 |

FOREIGN PATENT DOCUMENTS

EP 2387298 A1 11/2011
EP 3 333 008 A1 6/2018

* cited by examiner

*Primary Examiner* — Alfonso Perez Borroto
(74) *Attorney, Agent, or Firm* — McGlew and Tuttle, P.C.

(57) ABSTRACT

A mobile measuring device (100) includes a power supply module (110) that includes a rechargeable battery (120), a primary battery (130) and an electronic control unit (140). The rechargeable battery is permanently installed in the mobile measuring device and can be charged via a charging device (122) of the mobile measuring device. The primary battery is also permanently installed in the mobile measuring device. The electronic control unit is configured to guarantee a power supply of the mobile measuring device via the rechargeable battery as long as an electrical minimum power supply is provided by the rechargeable battery and to change to a temporary power supply by the primary battery if the minimum supply power is undershot.

20 Claims, 4 Drawing Sheets

MOBILE MEASURING DEVICE WITH A POWER SUPPLY MODULE AND PROCESS FOR POWER SUPPLY

CROSS REFERENCE TO RELATED APPLICATIONS

This application claims the benefit of priority under 35 U.S.C. § 119 of German Application 10 2019 005 358.3, filed Jul. 31, 2019, the entire contents of which are incorporated herein by reference.

TECHNICAL FIELD

The present invention pertains to a mobile measuring device with a power supply module, as well as to a process for the power supply of a mobile measuring device.

TECHNICAL BACKGROUND

Using a rechargeable battery or primary battery for the power supply of a mobile measuring device is generally known. A rechargeable battery has the advantage that it can, in principle, be charged, whereas a primary battery cannot be reused after the power stored in it is used up.

Moreover, the use of an electronic control unit, by means of which it is possible to change between different power supply devices, is known.

Thus, EP 3 333 008 A1 describes an adaptive system for the management of a plurality of battery cells, which are connected to one another in a common circuit. In this case, the circuit changes the power supply between the plurality of battery cells as a function of a determined state of each of the battery cells.

SUMMARY

An object of the present invention is to make possible an improved power supply module, and in particular a power supply module with an especially long operating time of a mobile measuring device supplied therewith.

A mobile measuring device with a power supply module, wherein the power supply module has a rechargeable battery, a primary battery and an electronic control unit, is proposed according to the present invention for accomplishing this object.

The rechargeable battery is permanently installed (fixedly connected/fixedly installed) in the mobile measuring device and is chargeable via a charging device of the mobile measuring device.

The primary battery is likewise permanently installed (fixedly connected/fixedly installed) in the mobile measuring device.

The electronic control unit is configured to guarantee a power supply of the mobile gas measuring device via the rechargeable battery as long as an electrical minimum supply power is provided by the rechargeable battery and to change to a temporary power supply by the primary battery if the minimum supply power is undershot.

It was found within the framework of the present invention that charging of a permanently installed rechargeable battery via the charging device makes possible a longer operating time than this would be the case in case of a power supply guaranteed only via a primary battery. Furthermore, it was found that a temporary failure of the mobile measuring device could occur due to the running down of the rechargeable battery, so that the power supply has to be guaranteed via another power supply device in case of a depleted or almost depleted rechargeable battery. In this connection, the primary battery advantageously provides an especially safe power supply, since primary batteries typically have a longer operating time than a rechargeable battery.

A safer and more reliable operation can thus be made possible according to the present invention in case the mobile measuring device has to be used for a longer period than this would be possible due to only a power supply by the rechargeable battery.

The fact that the rechargeable battery and the primary battery are permanently installed according to the present invention means that a change of these two components of the power supply module is not intended from the mobile measuring device without additional aid. This especially means that there is no mechanism at the mobile measuring device which is directly configured to support the removal or the changing of one of these two components. This reduces the effort in case of the use of the mobile measuring device according to the present invention, since a manual change is not necessary. The rechargeable battery and the primary battery are preferably not detachably or only conditionally detachably installed within the mobile measuring device. Conditionally detachable in this case means that at least one auxiliary joint part or a soldered connection has to be destroyed in order to remove the corresponding object. In one embodiment according to the present invention, such a removal of the rechargeable battery or primary battery is preferably intended only for the disposal of these components.

Because the rechargeable battery and the primary battery are permanently installed, it is, moreover, guaranteed according to the present invention that the mobile measuring device is operated with the rechargeable battery and the primary battery and cannot be changed by a manual intervention to a less safe operation only with the rechargeable battery or only with the primary battery. Moreover, an especially safe mobile measuring device is provided because of the permanent installation of the rechargeable battery and the primary battery, since changing the primary battery or the rechargeable battery in potentially explosive areas can be dangerous. Because no change of these components is possible without additional aid, an unintentional occurrence of a potential explosion is also avoided.

The minimum supply power is a predefined minimum supply power. The minimum supply power in this case is typically the electrical power that is necessary to operate the mobile measuring device in a reliable manner.

The rechargeable battery in the power supply module can be advantageously dimensioned such that it guarantees operation of the mobile measuring device between two charging cycles. For example, the rechargeable battery may be configured to provide a 24-hour operation if a daily charging of the rechargeable battery via the charging device is intended. The rechargeable battery is configured in another example to provide a weekly operation if a weekly charging of the rechargeable battery via the charging device is intended. Thus, the primary battery would, as a general rule, not be used at all and would only be actuated by the electronic control unit in case of an unexpectedly long operation of the mobile measuring device.

Since the primary battery is only used during the intended operation of the mobile measuring device if the rechargeable battery is no longer providing the electrical minimum supply power, the fact that it is permanently installed does not represent a drawback. Mobile measuring devices often require a very low supply power, so that a sufficiently long lifetime of the primary battery can be guaranteed in case of an only occasional use of the primary battery. Sufficiently long in this case means that the durability of the power supply module according to the present invention can be at least comparable to the durability of other parts of the mobile measuring device, without a change being necessary for this from the rechargeable battery or the primary battery.

Moreover, the mobile measuring device according to the present invention also makes possible an operation after very long storage times, since the rechargeable battery has possibly run down during the long storage time, but the primary battery can still typically guarantee the power supply after a long storage time.

Primary batteries are typically also called batteries. The precise structure of a rechargeable battery and of a primary battery according to the present invention are generally known and will therefore not be explained in detail below.

The mobile measuring device according to the present invention comprises at least one rechargeable battery and at least one primary battery. In one embodiment according to the present invention, the mobile measuring device comprises a plurality of rechargeable batteries and/or a plurality of primary batteries, all of which are permanently installed within the mobile measuring device. In this embodiment, a change is made by the electronic control unit to a supply by the one primary battery or the plurality of primary batteries if the minimum power supply by the one rechargeable battery or by the plurality of rechargeable batteries is undershot.

The electronic control unit may be configured in the form of a circuit board. The electronic control unit may, furthermore, have a computer for carrying out a comparison of the electrical supply power with the electrical minimum supply power. The electronic control unit has according to the present invention a storage unit that is configured to store the predefined electrical minimum supply power and to output it for a comparison with the current electrical supply power.

Preferred embodiments of the mobile measuring device according to the present invention will be described below.

In an especially preferred embodiment, the primary battery can be operated in a broader temperature range than the rechargeable battery. In particular, the primary battery can preferably be operated in a lower and/or higher temperature range than the rechargeable battery in this embodiment. In this embodiment, the primary battery guarantees that a power supply of the mobile measuring device by the primary battery is guaranteed even in temperature ranges, in which the rechargeable battery is no longer functioning structurally. Consequently, the mobile measuring device can be used in a temperature range, in which a measuring device supplied via a rechargeable battery can no longer be used. A rechargeable battery typically functions in a temperature range between $-20°$ C. and $50°$ C. Hence, this embodiment is advantageous for the use of the mobile measuring device in very cold regions, for example, in a polar region, and/or in very hot regions, for example, in a coastal region.

In another, especially preferred embodiment, the primary battery is a lithium primary battery, and in particular a lithium thionyl chloride primary battery. A lithium thionyl chloride battery can typically be operated in a temperature range between $-50°$ C. and $85°$ C. Therefore, an operation of a correspondingly supplied mobile measuring device can be guaranteed both in very hot regions and in very cold regions in this variant of the embodiment. In another variant of this embodiment, the lithium primary battery is a lithium iron sulfide primary battery, a lithium iodine primary battery, a lithium manganese dioxide primary battery, a lithium sulfur dioxide primary battery or a lithium carbon monofluoride primary battery. Each of these alternatives for the lithium primary battery has its own specific temperature range, in which the corresponding primary battery can be operated.

In an alternative embodiment, the primary battery used is an alkaline manganese primary battery, an aluminum-air primary battery, a nickel oxyhydroxide primary battery, a mercury oxide-zinc primary battery, a silver oxide-zinc primary battery, a zinc-carbon primary battery, a zinc chloride primary battery or a zinc-air primary battery. Each of these alternatives has its own specific temperature range, in which the corresponding primary battery can be operated.

In an advantageous embodiment, the electronic control unit is further configured to change back from the temporary power supply by the primary battery to the power supply by the rechargeable battery if the minimum supply power can again be provided by the rechargeable battery. In this embodiment, it is automatically guaranteed that a long-lasting supply of the mobile measuring device via the permanently installed primary battery is not unintentionally provided, as a result of which the primary battery would be depleted unnecessarily rapidly. In an alternative or additional embodiment, the end of a charging operation of the rechargeable battery via the charging device is detected and a change is then made back to the power supply by the rechargeable battery.

In another embodiment, the charging device of the mobile measuring device comprises an electrical plug-in connection that has a receptacle for a charging cable of an external supply device. Such a charging device can be provided in an especially advantageous manner. The electronic control unit is configured in a variant of this embodiment to detect whether a charging cable is connected to the electrical plug-in connection and to control the power supply as a function of this detection. For example, a change can be made to the power supply by the primary battery if the charging cable is detected in the plug-in connection. In an alternative or additional example of this variant, a change is, furthermore, made to a power supply by the rechargeable battery if the separation of the charging cable from the electrical plug-in connection is detected.

In another embodiment, the charging device of the mobile measuring device comprises a solar module. Depending on the area of use of the mobile measuring device, a long-lasting operation of the power supply module according to the present invention in a sunny region can be guaranteed in an especially safe manner by means of the solar module. The charging device in a variant of this embodiment comprises, in addition to the solar module, an electrical plug-in connection and/or an induction module. In this variant, the solar module makes possible an alternative or additional charging operation in addition to a conventional charging via an electrical plug-in connection or an induction module.

In another embodiment, the charging device of the mobile measuring device comprises an induction module. In this embodiment, electronic components of the mobile measuring device can especially certainly be prevented from coming into contact with the surrounding area of the measuring device. This is especially advantageous for a use of the mobile measuring device in a potentially explosive area. Mobile measuring devices typically consume very little current, namely less than 0.3 mA, especially less than 0.1 mA, preferably about 0.05 mA. Therefore, only a low charging current needs to be provided via the induction module as well. A charging current between 10 mA and 100 mA, preferably about 50 mA, is preferably provided via the induction module. Depending on the ratio between the charging current and the average consumption of the mobile measuring device, a charging time of a few minutes per day may already be sufficient in order to provide a sufficient power supply of the mobile measuring device according to the present invention.

In another embodiment, the electronic control unit is further configured to switch off the mobile measuring device if at least one switch-off condition of a group of switch-off conditions was detected by means of a corresponding detection device of the mobile measuring device. As a result, a low power consumption of the mobile measuring device can be made possible, which additionally extends the operation time of the power supply module according to the present invention.

In an especially preferred variant of the previous embodiment, the group of switch-off conditions comprises the detection of a continuous absence of movement, the detection of a predefined current time, the detection of a predefined position and/or the detection of a charging operation of the rechargeable battery. These switch-off conditions are especially reliably detectable switch-off conditions, so that an unintentional switching off of the mobile measuring device is avoided. The detection of the switch-off condition of this group of switch-off conditions preferably takes place via a detection device of the mobile measuring device. Examples of such a detection device are an acceleration sensor, an optical sensor, a vibration sensor, a temperature sensor, a tilt switch, a GPS sensor, a radio module, an induction module and/or a timer. The manner of functioning of this detection device is generally known and will therefore not be explained in detail below.

In an especially preferred embodiment, the mobile measuring device is a mobile gas measuring device. The mobile gas measuring device includes a gas measuring unit with features such as disclosed in the mobile gas measuring devices of U.S. Pat. Nos. 7,395,692 , 10,191,023 (the entire contents of U.S. Pat. Nos. 7,395,692 ,10,191,023 are incorporated herein by reference). In this embodiment, the fact that only a very low average power consumption is present for the duration of the operation of the mobile measuring device is especially advantageously made use of according to the present invention. The average consumption of the mobile gas measuring device in this embodiment is typically between 0.02 mA and 1 mA, especially between 0.03 mA and 0.2 mA, preferably about 0.05 mA. Therefore, only a charging time of a few minutes is necessary for a full charge of the rechargeable battery in case of a charging current of 50 mA. The primary battery thus hardly needs to be used because of the rapid charging. As a result, the power supply module according to the present invention can make possible an especially long operating time of the mobile gas measuring device. Furthermore, it is advantageous in this embodiment that a mobile gas measuring device is typically not in use on an ongoing basis, so that there are times, at which a charging of the mobile gas measuring device may be meaningful, for example, during a maintenance mode, especially during a gasification test, during a calibration, during a device test and/or during a device communication for test purposes. Furthermore, gas measuring devices are typically stored at predefined times of the day, for example, at night, so that a charging of the rechargeable battery can take place during a storage of the gas measuring device, especially outside of a measuring operation.

The rechargeable battery and/or the primary battery are preferably permanently installed in the mobile measuring device such that a screw connection has to be loosened in order to remove and/or to change the rechargeable battery and/or the primary battery.

According to another aspect of the present invention, a process for the power supply of a mobile measuring device is proposed for accomplishing the above-mentioned object. In this case, the process according to the present invention has the following steps:

permanent installation of a rechargeable battery in the mobile measuring device such that the rechargeable battery can be charged via a charging device of the mobile measuring device, permanent installation of a primary battery in the mobile measuring device, controlling of a power supply of the mobile measuring device such that the power supply of the mobile measuring device is guaranteed via the rechargeable battery as long as an electrical minimum power supply is provided by the rechargeable battery, and changing to a temporary power supply by the primary battery if the minimum power supply is undershot.

The process according to the present invention advantageously makes possible an especially reliable and long-lasting power supply of the mobile measuring device. Thus, a chargeable power supply, which is protected by the primary battery, is provided by the use of the rechargeable battery. Such a protection may be necessary, for example, during a charging operation.

Permanent installation means according to the present invention such an installation that a user of the process cannot remove and/or change the primary battery and the rechargeable battery without additional aid. The primary battery and the rechargeable battery are preferably permanently installed such that the change and/or the removal of the primary battery and/or of the rechargeable battery are not possible without the partial destruction of an auxiliary joint part or of a soldered connection.

The primary battery can be used in a broader temperature range than the rechargeable battery in an especially preferred embodiment of this process according to the present invention. As a result, the power supply of the mobile measuring device can also be provided in very cold or very hot regions of use.

In another advantageous embodiment, the process according to the present invention further comprises a changing back from the temporary power supply by the primary battery to the power supply by the rechargeable battery if the minimum supply power can again be provided by the rechargeable battery. In this embodiment, a change is advantageously made in an automated manner between the primary battery and the rechargeable battery as the device of the power supply.

The present invention shall now be explained in more detail on the basis of advantageous exemplary embodiments schematically shown in the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
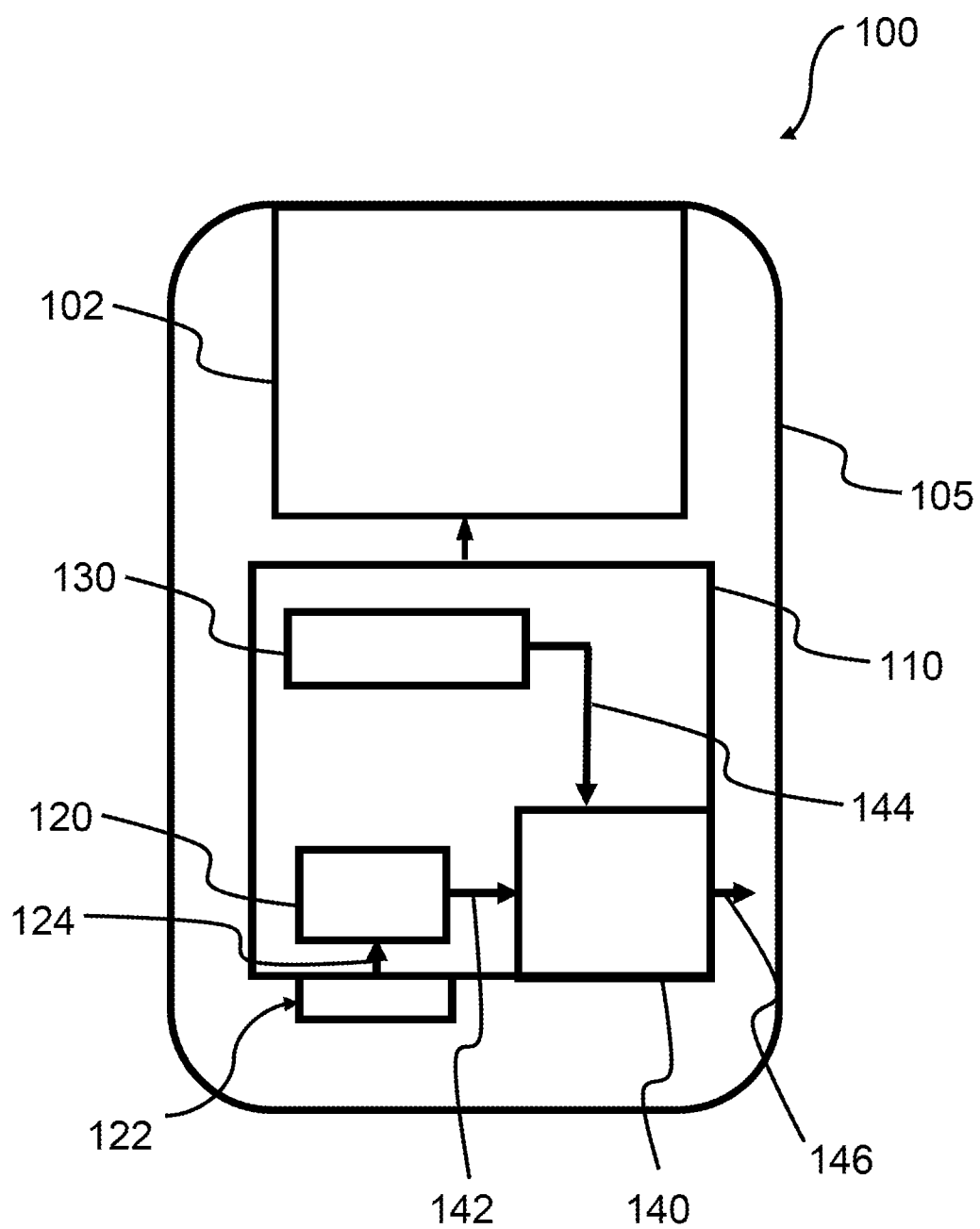
FIG. 1 is a schematic view of a first exemplary embodiment of a mobile measuring device according to the present invention.

Referring to the drawings, FIG. 1 shows a schematic view of a first exemplary embodiment of a mobile measuring device 100 according to the present invention. The mobile measuring device 100 has a power supply module 110, which comprises a rechargeable battery 120, a primary battery 130 and an electronic control unit 140. In the exemplary embodiment being shown, the mobile measuring device 100 is a mobile gas measuring device with gas measuring unit 102. In one exemplary embodiment, not shown, the mobile measuring device is an optical measuring device or a sound measuring device. The mobile measuring device 100 shown displays via an output unit (not shown) a measured gas concentration of a gas to be measured. In one exemplary embodiment, not shown, the mobile measuring device comprises a radio unit via which a radio signal is provided that indicates the measured values being measured, especially the measured gas concentrations.

The power supply module 110 is entirely arranged within a housing 105 of the mobile measuring device 100.

The rechargeable battery 120 is permanently installed in the mobile measuring device 100. In the exemplary embodiment shown, the rechargeable battery 120 is permanently fastened to an internal structure of the housing 105 via a soldered connection. In one exemplary embodiment, not shown, the rechargeable battery is permanently installed within the mobile measuring device via a bonded connection or welded connection. In another exemplary embodiment, not shown, the rechargeable battery is permanently installed within the mobile measuring device via an auxiliary joint part such that the auxiliary joint part has to be destroyed in order to remove the rechargeable battery from the mobile measuring device. In another exemplary embodiment, not shown, the rechargeable battery is permanently installed by a screw connection. According to the present invention, no removing device, which simplifies manual removal of the rechargeable battery 120, is provided at the mobile measuring device 100. According to the present invention, the housing 105 may consequently be configured such that no electronic component is freely accessible, as a result of which an operation is also possible in a potentially explosive area. Furthermore, the rechargeable battery 120 can be charged via a charging device 122 of the mobile measuring device 100. The charging device 122 has for this purpose an electrical feed line 124 to the rechargeable battery 120. The charging device 122 may be arranged outside of the power supply module 110, as this is the case in the exemplary embodiment shown. The charging device 122 is, in the exemplary embodiment shown, an inductive charging device, which comprises an induction module. The rechargeable battery 120 of the mobile measuring device 100 can consequently be charged with a charging device without an electronic contact.

The primary battery 130 is likewise permanently installed in the mobile measuring device 100. In the exemplary embodiment shown, the primary battery 130 is permanently fastened to the internal structure of the housing 105 via a soldered connection. In one exemplary embodiment, not shown, the primary battery is permanently installed within the mobile measuring device via a bonded connection or via a welded connection. In another exemplary embodiment, not shown, the primary battery is permanently installed via an auxiliary joint part within the mobile measuring device such that the auxiliary joint part has to be destroyed in order to remove the primary battery from the mobile measuring device. In another exemplary embodiment, not shown, the rechargeable battery is permanently installed by a screw connection within the mobile measuring device. According to the present invention, no removing device, which simplifies manual removal of the primary battery 130, is provided at the mobile measuring device 100. In the exemplary embodiment shown, the primary battery is a lithium primary battery. Especially advantageously, the lithium primary battery is a lithium thionyl chloride primary battery. This lithium primary battery has a temperature range in which it can be used for the power supply of the mobile measuring device that is especially broad compared to the usual temperature range of rechargeable batteries of between −20° C. and 50° C. The use of a primary battery 130, which has a greater usable temperature range than the rechargeable battery 120, is especially advantageous since the mobile measuring device can consequently also be used at temperatures, which would not be possible by the rechargeable battery 120. In an alternative exemplary embodiment, not shown, it is a different lithium primary battery, e.g., a lithium iron sulfide primary battery, a lithium iodine primary battery, a lithium manganese dioxide primary battery, a lithium sulfur dioxide primary battery or a lithium carbon monofluoride primary battery. In another, alternative exemplary embodiment, not shown, the primary battery is an alkaline manganese primary battery, an aluminum-air primary battery, a nickel-oxyhydroxide primary battery, a mercury oxide-zinc primary battery, a silver oxide-zinc primary battery, a zinc-carbon primary battery, a zinc chloride primary battery or a zinc-air primary battery. In another exemplary embodiment, not shown, the mobile measuring device has a plurality of rechargeable batteries and/or a plurality of primary batteries.

The electronic control unit 140 is configured to ensure a power supply of the mobile gas measuring device 100 via the rechargeable battery 120 as long as an electrical minimum supply power is provided by the rechargeable battery 120 and to change to a temporary power supply by the primary battery 130 if the minimum supply power is undershot. For the comparison between the currently provided electrical supply power and the predefined electrical minimum supply power, the electronic control unit 140 is connected to the rechargeable battery 120 via a first electrical connection 142. In order to change the current power supply to the temporary power supply by the primary battery 130, the electronic control unit 140 is connected via a second electrical connection 144 to the primary battery 130. In the exemplary embodiment being shown, the electronic control unit 140 provides the electrical supply signal 146, which supplies the mobile measuring device 100 with power. In one exemplary embodiment, not shown, the electronic control unit controls the power supply by the power supply module such that the electronic supply signal is sent directly from the primary battery or from the rechargeable battery to a corresponding electronic unit of the mobile measuring device, which electronic unit is to be supplied with power. In the exemplary embodiment being shown, the electronic control unit 140 comprises a power measuring device (not shown), which is configured to measure a power present at the power measuring device. Furthermore, the electronic control unit 140 is configured to compare the measured power with the predefined electrical minimum supply power and to control the power supply according to the present invention. For this comparison, the electronic control unit 140 includes has a storage unit (not shown), in which the predefined minimum supply power is stored.

The mobile gas measuring device can advantageously be charged during a storage between two uses. In another example, the mobile gas measuring device has a separate maintenance mode or charging mode, during which a charging of the gas measuring device can advantageously be carried out.

Figure 2:
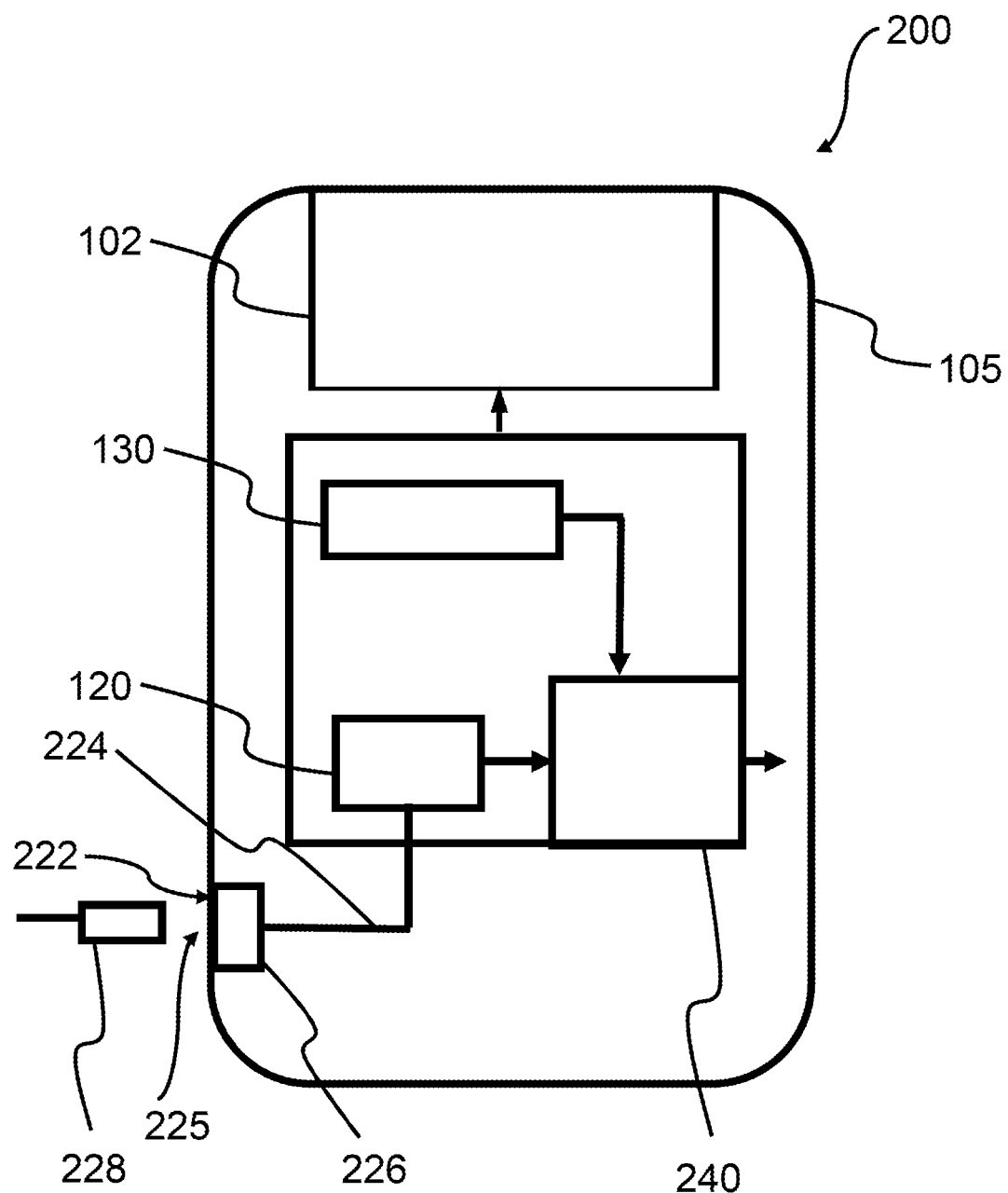
FIG. 2 is a schematic view of a second exemplary embodiment of a mobile measuring device according to the present invention.

FIG. 2 shows a schematic view of a second exemplary embodiment of a mobile measuring device 200 according to the present invention.

The mobile measuring device 200 differs from the mobile measuring device 100 shown in FIG. 1 by the charging device 222 comprising an electrical plug-in connection 225, which has a receptacle 226 for a charging cable 228 of an external supply device. The electrical feed line 224 for the supply of the rechargeable battery 120 is correspondingly configured between the receptacle 226 and the rechargeable battery 120. The receptacle 226 comprises an opening in the housing 105 of the mobile measuring device 200, into which the charging cable 228 has to be inserted for charging the rechargeable battery 120.

In one exemplary embodiment, not shown, the electronic control unit of the mobile measuring device is configured such that it detects a currently present charging operation via a charging cable located in the receptacle and guarantees temporary power supply by the primary battery during the charging operation. The detection of a currently present charging operation takes place, for example, via a detection of an electrical supply power provided by the rechargeable battery or via an optical sensor or via another suitable detection unit for detecting a charging cable plugged into the receptacle.

The mobile measuring device 200 differs, moreover, from the mobile measuring device 100 shown in FIG. 1 by the electronic control unit 240 being additionally configured to change back from the temporary power supply by the primary battery 130 to the power supply by the rechargeable battery 120 if the minimum supply power can again be provided by the rechargeable battery 120. As a result, the electronic control unit 240 makes possible a change of the power supply from the rechargeable battery 120 to the primary battery 130 and back again. In an alternative exemplary embodiment, not shown, the electronic control unit is configured to change back from the temporary power supply by the primary battery to the power supply by the rechargeable battery if a detected charging operation of the rechargeable battery is completed or finished.

Figure 3:
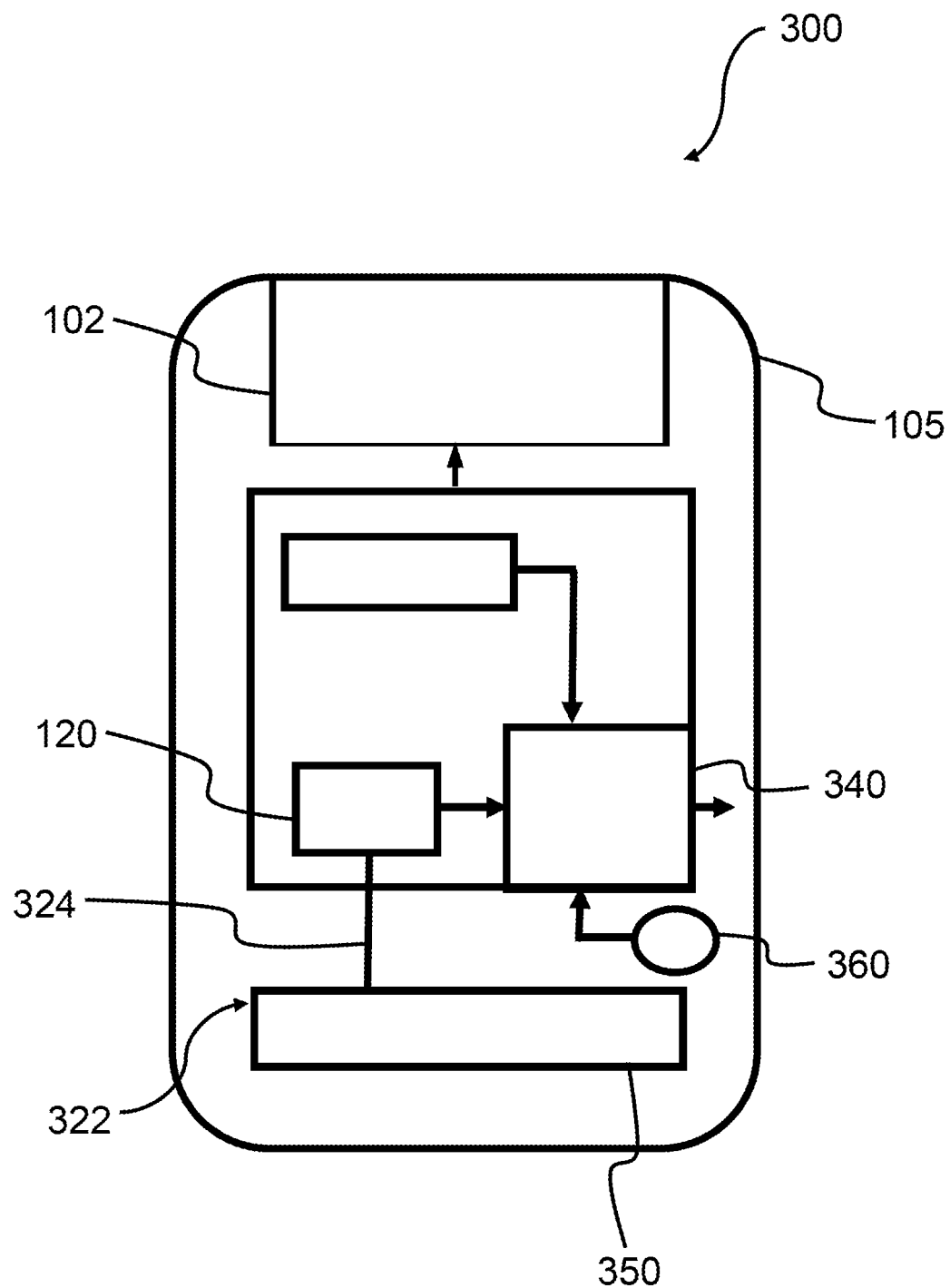
FIG. 3 is a schematic view of a third exemplary embodiment of a mobile measuring device according to the present invention.

FIG. 3 shows a schematic view of a third exemplary embodiment of a mobile measuring device 300 according to the present invention.

The mobile measuring device 300 differs from the mobile measuring devices 100, 200 shown in FIG. 1 and FIG. 2 by the charging device 322 of the mobile measuring device 300 comprising a solar module 350. The solar module 350 is connected to the rechargeable battery 120 via the electrical feed line 324. The use of the solar module 350 advantageously makes possible a charging of the rechargeable battery 120 during an operation of the mobile measuring device 300. The use of the solar module 350 makes it possible, furthermore, to avoid an electrical contacting of the mobile measuring device 300 from outside and therefore a use of the measuring device 300 in a potentially explosive area.

In one exemplary embodiment, not shown, a storage system is provided, which illuminates the mobile measuring device during a storage, for example, between two uses, and as a result makes possible a contactless charging of the rechargeable battery of the mobile measuring device. The illumination can take place by LED light in this exemplary embodiment. Since the time between two uses of the mobile measuring device is typically several hours, the typically low power consumption per minute in case of solar cells is sufficient to make possible a full charging of the rechargeable battery during the storage.

Furthermore, the mobile measuring device 300 differs from the mobile measuring devices 100, 200 shown in FIG. 1 and FIG. 2 by it having, furthermore, a detection device 360, which is connected to the electronic control unit 340 and is configured to detect a continuous absence of movement. The detection device 360 is an acceleration sensor in the present case. The electronic control unit 340 is additionally configured in this case to switch off the mobile measuring device if a continuous absence of movement was detected by the detection device 360. In one exemplary embodiment, not shown, an alternative or additional switch-off condition is detected by the electronic control unit. Examples of such a switch-off condition are the detection of a predefined time, the detection of a predefined position and/or the detection of a charging operation of the rechargeable battery.

In one exemplary embodiment, not shown, a central control unit of the mobile measuring device rather than the electronic control unit of the power supply module is connected to the corresponding detection device.

According to the present invention, the detection device 360 is arranged within the housing 105 of the mobile measuring device 300.

Figure 4:
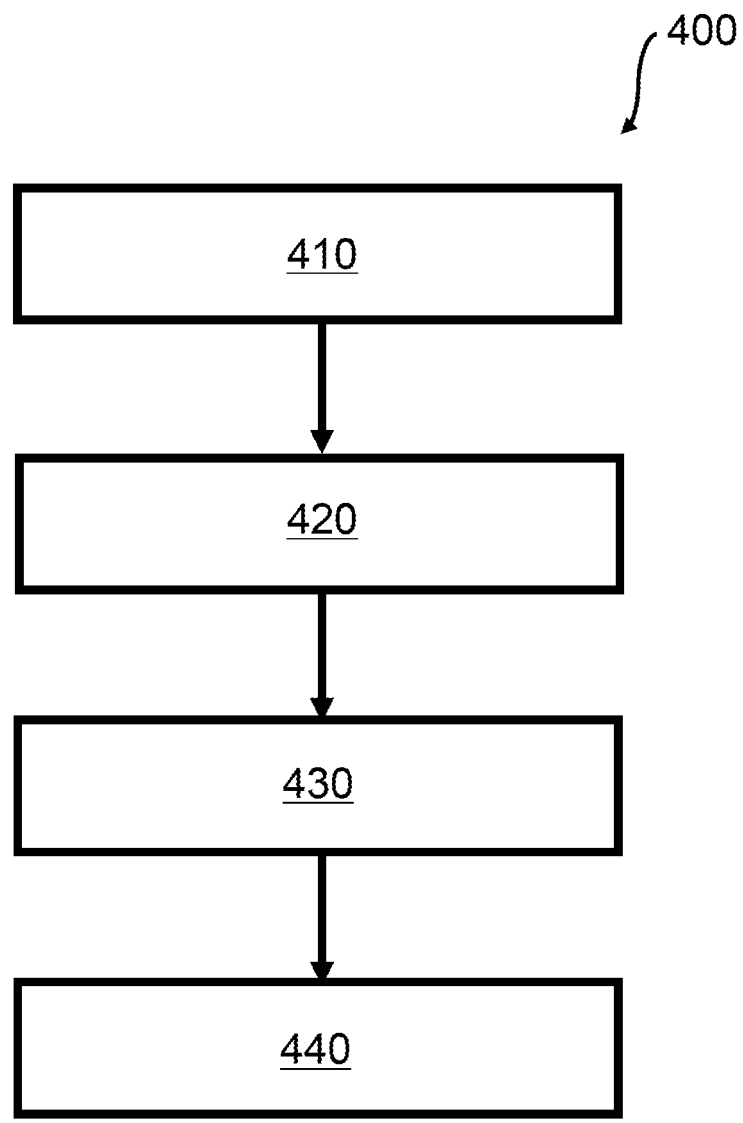
FIG. 4 is a flow chart of an exemplary embodiment of a process according to another aspect of the present invention.

FIG. 4 shows a flow chart of an exemplary embodiment of a process 400 according to another aspect of the present invention.

The process 400 according to the present invention for the power supply of a mobile measuring device has the steps described below.

A first step 410 comprises a permanent installation of a rechargeable battery in the mobile measuring device such that the rechargeable battery can be charged via a charging device of the mobile measuring device.

A next step 420 comprises a permanent installation of a primary battery in the mobile measuring device.

A next step 430 comprises a controlling of the power supply of the mobile measuring device such that the power supply of the mobile measuring device is guaranteed via the rechargeable battery as long as an electrical minimum power supply is provided by the rechargeable battery.

A further step 440 comprises a changing to a temporary power supply by the primary battery if the minimum power supply is undershot.

The two steps 410 and 420 are carried out during the manufacture of the mobile measuring device according to the present invention. In particular, no changing and hence also no manual installation of the rechargeable battery or of the primary battery by a user of the mobile measuring device is intended.

Step 430 is carried out on an ongoing basis or at regular intervals during the operation of the mobile measuring device in order to thereby monitor the electrical supply power provided.

Step 440 is carried out only in case it is determined during step 430 that the electrical minimum supply power was undershot.

In an additional exemplary embodiment, the process comprises an additional step, which is carried out after step 440. This additional step comprises a changing back from the temporary power supply by the primary battery to the power supply by the rechargeable battery if the electrical minimum supply power can again be provided by the rechargeable battery. In this additional exemplary embodiment, step 430 is carried out again as soon as the additional step was carried out. In this case, steps 430, 440 and the additional step are always carried out in this sequence, so that the power supply of the mobile measuring device is always provided via the rechargeable battery in case of a sufficiently charged rechargeable battery.

While specific embodiments of the invention have been shown and described in detail to illustrate the application of the principles of the invention, it will be understood that the invention may be embodied otherwise without departing from such principles.

LIST OF REFERENCE NUMBERS

100, 200, 300 Mobile measuring device
102 Gas measuring unit
105 Housing
110 Power supply module
120 Rechargeable battery
122, 222, 322 Charging device
124, 224, 324 Electrical feed line
130 Primary battery
140, 240, 340 Electronic control unit
142 First electrical connection
144 Second electrical connection
146 Electrical supply signal
225 Electrical plug-in connection
226 Receptacle
228 Charging cable
350 Solar module
360 Detection device
400 Process
410, 420, 430, 440 Process steps

What is claimed is:

1. A mobile measuring device comprising:
a charging device;
a power supply module, the power supply module comprising:
a rechargeable battery permanently installed in the mobile measuring device, the rechargeable battery being connected to the charging device and being configured to be charged via the charging device;
a primary battery permanently installed in the mobile measuring device; and
an electronic control unit configured to guarantee a power supply of the mobile measuring device via the rechargeable battery as long as an electrical minimum supply power is provided by the rechargeable battery and to change to a temporary power supply by the primary battery if the electrical minimum supply power is undershot.

2. A mobile measuring device in accordance with claim 1, wherein the primary battery is configured to operate in a broader temperature range than the rechargeable battery.

3. A mobile measuring device in accordance with claim 1, wherein the electronic control unit is further configured to change back from the temporary power supply by the primary battery to the power supply by the rechargeable battery if the minimum supply power is again providable by the rechargeable battery.

4. A mobile measuring device in accordance with claim 1, wherein the primary battery is a lithium primary battery.

5. A mobile measuring device in accordance with claim 1, wherein the charging device comprises an electrical plug-in connection comprising a receptacle for a charging cable of an external supply device.

6. A mobile measuring device in accordance with claim 1, wherein the charging device of the mobile measuring device comprises a solar module.

7. A mobile measuring device in accordance with claim 1, wherein the charging device of the mobile measuring device comprises an induction module.

8. A mobile measuring device in accordance with claim 1, further comprising detection device configured to detect any of a group of switch-off conditions, wherein the electronic control unit is further configured to switch off the mobile measuring device if at least one switch-off condition of the group of switch-off conditions is detected by the detection device.

9. A mobile measuring device in accordance with claim 8, wherein the group of switch-off conditions comprises a detection of a continuous absence of movement, a detection of a predefined current time, a detection of a predefined position and/or a detection of a charging operation of the rechargeable battery.

10. A mobile measuring device in accordance with claim 1, further comprising a gas measuring unit, wherein the mobile measuring device is a mobile gas measuring device.

11. A process for a power supply of a mobile measuring device, the process comprising the steps of:
fixedly installing a rechargeable battery in the mobile measuring device such that the rechargeable battery can be charged via a charging device of the mobile measuring device;
fixedly installing a primary battery in the mobile measuring device;
controlling a power supply of the mobile measuring device such that the power supply of the mobile measuring device is guaranteed via the rechargeable battery as long as an electrical minimum power supply is provided by the rechargeable battery, and changing to a temporary power supply by the primary battery if the minimum power supply is undershot.

12. A process in accordance with claim 11, wherein the rechargeable battery is fixedly installed in the mobile measuring device via one of a soldered connection, a welding connection and a bonded connection.

13. A process in accordance with claim 11, wherein the rechargeable battery is fixedly installed in the mobile measuring device via an auxiliary joint part such that the auxiliary joint part has to be destroyed in order to remove the rechargeable battery from the mobile measuring device.

14. A process in accordance with claim 11, wherein the primary battery is configured to operate in a broader temperature range than the rechargeable battery.

15. A process in accordance with claim 11, wherein the mobile measuring device is supplied with power only by the rechargeable battery when the electrical minimum supply power is not undershot, the mobile measuring device being provided with the temporary power supply exclusively by the primary battery when the minimum power supply is undershot.

16. A process in accordance with claim 11, wherein the primary battery is not rechargeable.

17. A process in accordance with claim 11, wherein the mobile measuring device is a mobile gas measuring device.

18. A mobile measuring device in accordance with claim 1, wherein the rechargeable battery is permanently installed in the mobile measuring device via one of a soldered connection, a welding connection and a bonded connection.

19. A mobile measuring device in accordance with claim 1, wherein the rechargeable battery is permanently installed in the mobile measuring device via an auxiliary joint part such that the auxiliary joint part has to be destroyed in order to remove the rechargeable battery from the mobile measuring device.

20. A mobile measuring device in accordance with claim 1, wherein the primary battery is not rechargeable, the rechargeable battery being configured such that only the rechargeable battery supplies the power supply to the mobile measuring device when the electrical minimum supply power is not undershot, the primary battery being configured such that only the primary battery supplies the power supply to the mobile measuring device when the minimum power supply is undershot.

* * * * *